US012539405B2

(12) United States Patent
Uzzo

(10) Patent No.: US 12,539,405 B2
(45) Date of Patent: Feb. 3, 2026

(54) Hematostick/HematoDart

(71) Applicant: Institute For Cancer Research, Philadelphia, PA (US)

(72) Inventor: Robert G. Uzzo, Philadelphia, PA (US)

(73) Assignee: INSTITUTE FOR CANCER RESEARCH, Philadelphia, PA (US)

( * ) Notice: Subject to any disclaimer, the term of this patent is extended or adjusted under 35 U.S.C. 154(b) by 751 days.

(21) Appl. No.: 17/271,703

(22) PCT Filed: Aug. 25, 2019

(86) PCT No.: PCT/US2019/048052

§ 371 (c)(1),
(2) Date: Feb. 26, 2021

(87) PCT Pub. No.: WO2020/046769

PCT Pub. Date: Mar. 5, 2020

(65) Prior Publication Data

US 2021/0316122 A1 Oct. 14, 2021

Related U.S. Application Data

(60) Provisional application No. 62/723,628, filed on Aug. 28, 2018.

(51) Int. Cl.
*A61M 35/00* (2006.01)
*A61B 17/00* (2006.01)

(52) U.S. Cl.
CPC ..... *A61M 35/003* (2013.01); *A61B 17/00491* (2013.01)

(58) Field of Classification Search
CPC ........... A61M 35/003; A61B 17/00491; A61B 2017/00004; A61B 2017/0061; A61B 2017/00623; A61B 2017/0065; A61B 2017/00659; A61B 2017/00907; A61B 17/0057; A61B 2017/308; A61B 17/00; A61F 17/00
See application file for complete search history.

(56) References Cited

U.S. PATENT DOCUMENTS 8,702,751 B2 * 4/2014 Stenton ............ A61B 17/00491 606/214
2007/0293831 A1 12/2007 Kwochka
2009/0105672 A1 * 4/2009 Cascio ................ A61M 35/003 604/310
2010/0160897 A1 6/2010 Ducharme et al.
2013/0004229 A1 * 1/2013 Kirk, III ............... B05B 11/048 401/160
2014/0221943 A1 8/2014 Carrara et al.
2016/0000418 A1 * 1/2016 Nakajima ............. A61M 39/22 606/214
2016/0095756 A1 4/2016 Zurovcik
2016/0303359 A1 10/2016 Bayly et al.
2018/0093082 A1 * 4/2018 Adams ................ A61M 35/006
2018/0264507 A1 * 9/2018 Hiemer ............... B05C 17/0126

* cited by examiner

*Primary Examiner* — Nicholas J. Weiss
*Assistant Examiner* — Gabriella E Burnette
(74) *Attorney, Agent, or Firm* — Ballard Spahr LLP

(57) ABSTRACT

The present disclosure provides hemostatic agent applicators configured to deliver hemostatic agents to an internal or external bleeding surface for promoting the clotting of blood, and to methods of using the applicator, and to kits comprising the applicator.

14 Claims, 2 Drawing Sheets

Hematostick/HematoDart

FIELD

The present disclosure is directed, in part, to hemostatic agent applicators configured to deliver one or more hemostatic agents to an internal or external bleeding surface for promoting the clotting of blood, to methods of using the applicator, and to kits comprising the applicator.

BACKGROUND

The need for urgent hemostasis is universal in surgery. Hemostasis is important for survival. Among other physiological impairments, hemostasis prevents cardiovascular instability, benefits wound healing, and decreases future infections. Hemostatic agents (materials) have been widely used as medicinal supplies or medical equipment in surgical operations, and the usefulness thereof has been well established. While mechanical suturing, clips, and staples remain the mainstay of bleeding prevention, they are not always practical once bleeding is encountered, particularly during laparoscopic/robotic and endoscopic procedures where bleeding decreases visualization of already small operative fields and access for larger instruments is limited.

In response to this need, the field of intraoperative hemostatic adjuncts continues to increase and improve. The number of various agents to help either provide a lattice to encourage hemostatis and/or activate the clotting cascade continues to grow as does their clinical effectiveness. Many of these agents, however, are applied manually and then held in place, usually under a gauze or sponge, thereby holding direct pressure on the bleeding wound. This practice poses several inefficiencies, including directionality and accuracy of placement and maintenance of position over the bleeding tissue. Moreover, given that the hemostatic agents cannot be completely confined to the target tissue, the initial application may result in waste and/or ineffective positioning, potentially leading to failure to control the bleeding. In addition, maintaining applied focal pressure to the bleeding surface over time is a key component to successful use of hemostatic agent. This is often achieved using various instruments to apply pressure to the area and can include continuous manual pressure using a finger, hand, or surgical instrument such as a suction device. Eventually, the pressure is released after what is believed to be the appropriate amount of time per the physician's discretion. This approach, however, can be problematic, because it often results in dislodgement of the hemostatic fabric and/or semisolid agent with the result of the initiation of re-bleeding. Thus, there is a need for improved methods of delivering hemostatic agents to patients.

SUMMARY

The present disclosure provides hemostatic agent applicators comprising: a handle having a proximal portion and a distal end; a delivery component located at the distal end of the handle; a first actuator located along the handle near the proximal portion of the handle, wherein the first actuator is configured to, upon engagement, release the delivery component from the distal end of the handle; and a second actuator located along the handle near the proximal portion of the handle, wherein the second actuator is configured to, upon engagement, release any contents of the delivery component.

The present disclosure also provides kits comprising: one or more hemostatic agent applicators, wherein the applicator comprises: a handle having a proximal portion and a distal end; a first actuator located at the proximal portion of the handle, wherein the first actuator is configured to, upon engagement, release a delivery component from the distal end of the handle; and a second actuator located at the proximal portion of the handle, wherein the second actuator is configured to, upon engagement, release any contents of the delivery component; and one or more delivery components configured to be attached to the distal end of the handle of the applicator.

The present disclosure also provides methods of using the hemostatic agent applicator, the method comprising: a) contacting a bleeding or weakened wound or surface of a patient with the hemostatic agent applicator; b) applying manual pressure to the surface or wound, thereby attaching the delivery component to the surface or wound, wherein the delivery component comprises one or more hemostatic meshes or contains one or more hemostatic agents, or both; c) maintaining the contact and the pressure for a time sufficient for hemostasis to begin; and d) optionally, releasing the delivery component from the handle by engaging the first actuator, thereby leaving the delivery component attached to the wound or surface.

BRIEF DESCRIPTION OF THE DRAWINGS

The accompanying figures, which are incorporated in and constitute a part of this specification, illustrate several aspects and together with the description serve to explain the principles of the disclosure.

Figure 1:
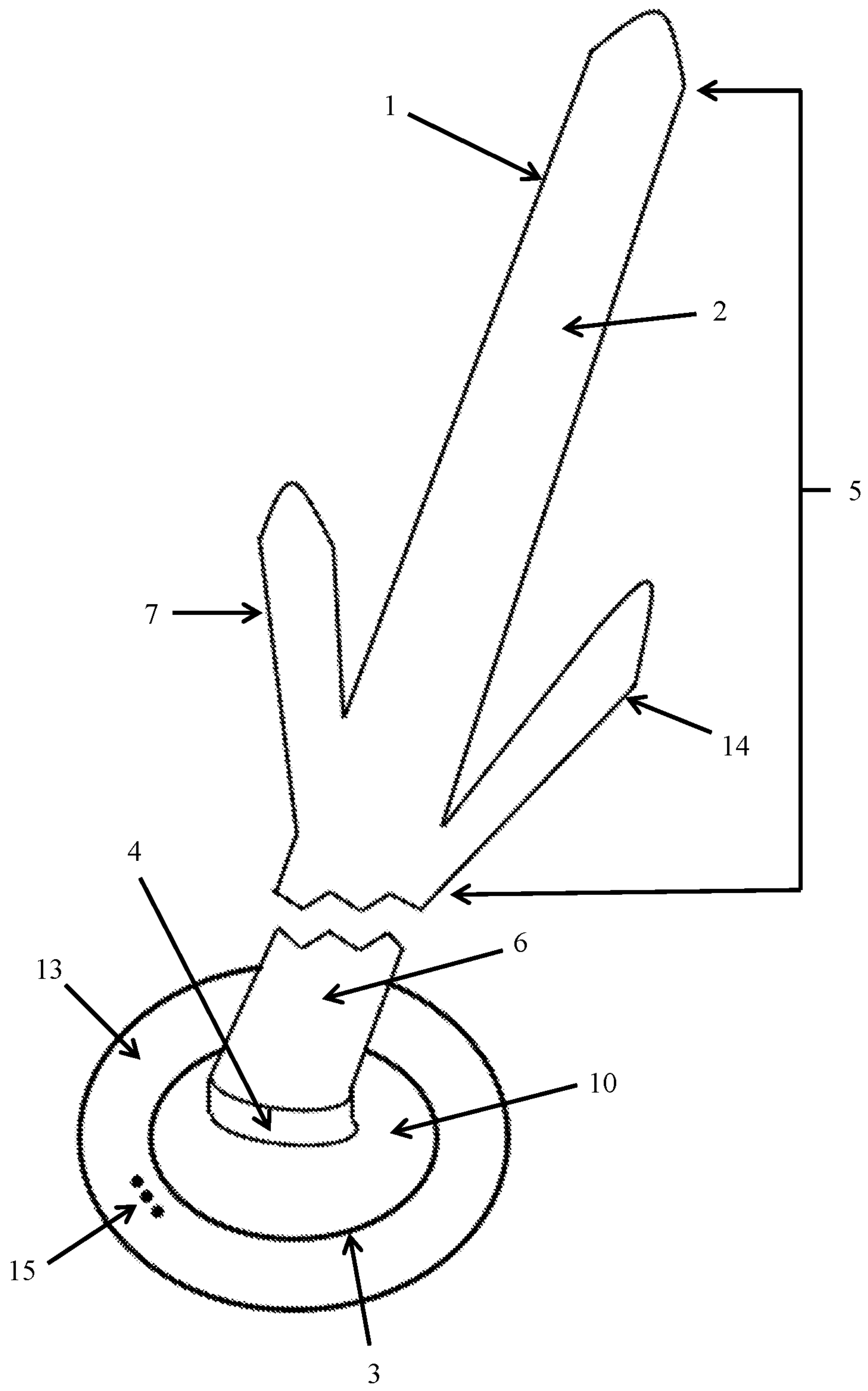
FIG. 1 shows an overall view of a representative hemostatic agent applicator according to one embodiment.

Additional features of the disclosure will be set forth in the description which follows, and will be apparent from the description, or can be learned by practice of the embodiments disclosed herein. The features of the disclosure can be realized and attained by means of the elements and combinations particularly pointed out in the appended claims. It is to be understood that both the foregoing general description and the following detailed description are exemplary and explanatory only and are not restrictive of the embodiments, as claimed.

DESCRIPTION OF EMBODIMENTS

The terminology used herein is for the purpose of describing particular embodiments only and is not intended to be limiting. Various terms relating to aspects of disclosure are used throughout the specification and claims. Such terms are to be given their ordinary meaning in the art, unless otherwise indicated. Other specifically defined terms are to be construed in a manner consistent with the definitions or uses provided herein.

As used herein, the singular forms "a," "an" and "the" include plural referents unless the context clearly dictates otherwise.

As used herein, "about" means that the recited numerical value is approximate and small variations would not significantly affect the practice of the disclosed embodiments. Where a numerical value is used, unless indicated otherwise by the context, "about" means the numerical value can vary by ±10% and remain within the scope of the disclosed embodiments.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The embodiments described herein may suitably "comprise", "consist of", or "consist essentially of", the steps, elements, and/or reagents described herein.

As used herein, the terms "subject" and "patient" are used interchangeably. A subject may include any animal, including mammals. Mammals include, but are not limited to, farm animals (e.g., horse, cow, pig), companion animals (e.g., dog, cat), laboratory animals (e.g., mouse, rat, rabbits), and non-human primates. In some embodiments, the subject is a human.

Unless otherwise expressly stated, it is in no way intended that any method set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

FIG. 1 shows an overall view of a representative hemostatic agent applicator according to one embodiment. Other design configurations can be contemplated by those skilled in the art based upon the features described herein. Referring to FIG. 1, a hemostatic agent applicator (1) comprises a handle (2) having a proximal portion (5) and a distal end (6). A delivery component (3) is located at the distal end of the handle. The handle of the applicator also comprises a first actuator (7), which in some embodiments is located at the proximal portion of the handle. The first actuator is configured to, upon engagement, release the delivery component (3) from the distal end of the handle. The handle of the applicator also comprises a second actuator (14), which in some embodiments is located at the proximal portion of the handle. The second actuator is configured to, upon engagement, release any contents of the delivery component (3).

In some embodiments, the hemostatic agent applicator (1) and/or the handle (2) is made of a material such as high strength plastic material, and/or metal. In some embodiments, the high strength plastic material is a tissue-friendly non-bioabsorbable polymer, copolymer, polymer mixture, or polymer alloy having sufficient strength to withstand without failure the torques and stresses that a hemostatic agent applicator would normally be subjected to in the body. Plastics generally suitable for use in medical instruments include, but are not limited to, polyetheretherketone (PEEK), epoxys, polyurethanes, polyesters, polyethylenes, vinyl chlorides, polysulfones, polytetrafluoro-ethylene (PTFE), polycarbonates, polyaryletherketone (PAEK), polyoxymethylene, nylon, carbon fiber polyester, polyetherketoneetherketoneketone (PEKEKK), silicones, and the like. Suitable metals include, but are not limited to, stainless steel, titanium alloys, including titanium-nickel, titanium-aluminum, and titanium-molybdenum alloys. In the embodiments in which the applicators are reusable, the manufacture materials can withstand sterilization procedures.

In some embodiments, the proximal end (5) of the handle (2) is configured for grasping by the operator's hand, and may be in the form of a handhold grip. In some embodiments, the handle (2) is flexible. As such, the handle can be manufactured from a material capable of being flexed or bent repeatedly without injury or damage to the handle. Numerous suitable flexible materials are known in the art and include, but are not limited to, medical grade polymers and/or co-polymers, such as polypropylene, polystyrene, polyurethane, polyvinylchloride, polyethylene, polyetheretherketone, polyetherimide, polyamides, polycarbonate, and biodegradables, or any combination thereof. Other medical grade polymers, metals, and metal alloys are also possible. In some embodiments, the handle (2) is made of a plastic disposable material or a solid material such that the handle can be reused. In some embodiments, the handle of the applicator is manufactured using a material that can withstand sterility procedures, such as autoclaving.

In some embodiments, the handle (2) is steerable. As such, all or a part of the handle can be configured to be guided in a number of directions (e.g., up, down, left, right, etc.) relative to another portion of the applicator (1). In some embodiments, the handle (2) contains one or more flexible joints allowing the handle to assume several shapes to reach a hemostatic agent application target area. Several types of flexible joints are known in the art, and include, but are not limited to, ball-and-socket joints, gimbal joints, hinge joints, and pivot joints. In some embodiments, multiple types of joints are present in the handle. In some embodiments, the handle comprises one flexible joint. In some embodiments, the handle comprises two flexible joints. In some embodiments, the handle comprises three flexible joints. In some embodiments, the handle comprises four flexible joints. In some embodiments, the handle comprises five flexible joints. In some embodiments, the handle comprises more than five flexible joints. In some embodiments, the handle (2) or the proximal portion (5) of the handle is configured for robotic or endoscopic operation, for example, adopted for attaching to a robotic arm or an endoscope.

The length of handle (2) ranges from about 2 cm to about 100 cm, from about 2 cm to about 90 cm, from about 2 cm to about 80 cm, from about 2 cm to about 70 cm, from about 2 cm to about 60 cm, from about 2 cm to about 50 cm, from about 2 cm to about 40 cm, from about 2 cm to about 30 cm, from about 3 cm to about 28 cm, from about 4 cm to about 26 cm, from about 6 cm to about 22 cm, from about 8 cm to about 20 cm, from about 10 cm to about 19 cm, from about 11 cm to about 18 cm, from about 12 cm to about 17 cm, from about 13 cm to about 16 cm, or from about 14 cm to about 15 cm. In some embodiments, the length of handle (2) ranges from about 3 cm to about 28 cm. In some embodiments, the length of handle (2) ranges from about 4 cm to about 26 cm. In some embodiments, the length of handle (2) ranges from about 6 cm to about 22 cm. In some embodiments, the length of handle (2) ranges from about 8 cm to about 20 cm. In some embodiments, the length of handle (2) ranges from about 10 cm to about 19 cm. In some embodiments, the length of handle (2) ranges from about 11 cm to about 18 cm. In some embodiments, the length of handle (2) ranges from about 12 cm to about 17 cm. In some embodiments, the length of handle (2) ranges from about 13 cm to about 16 cm. In some embodiments, the length of handle (2) ranges from about 14 cm to about 15 cm.

In some embodiments, the handle (2) is extendable (i.e., configured to be able to stretch out, or drawn to full length). In some embodiments, the handle (2) is telescopically extendable. In some embodiments, the handle (2) is composed of a plurality of segments joined via means of attachment well known in the art, such as, but not limited, to a screw thread or a snap-fit. In some embodiments, the handle (2) is extendable through addition of segments attached as described above. In some embodiments, the handle (2) is extendable up to 1.5-fold overall length as compared to the non-extended configuration. In some embodiments, the handle (2) is extendable up to overall 2-fold length as compared to the non-extended configuration. In some embodiments, the handle (2) is extendable up to overall 2.5-fold length as compared to the non-extended configuration. In some embodiments, the handle (2) is extendable up to overall 3-fold length as compared to the non-extended configuration. In some embodiments, the handle (2) is extendable up to overall 3.5-fold length as compared to the non-extended configuration. In some embodiments, the handle (2) is extendable up to overall 4-fold length as compared to the non-extended configuration. In some embodiments, the handle (2) is extendable up to overall 4.5-fold length as compared to the non-extended configuration. In some embodiments, the handle (2) is extendable up to overall 5-fold length as compared to the non-extended configuration. In some embodiments, the handle (2) is extendable up to overall more than 5-fold length as compared to the non-extended configuration.

Figure 2:
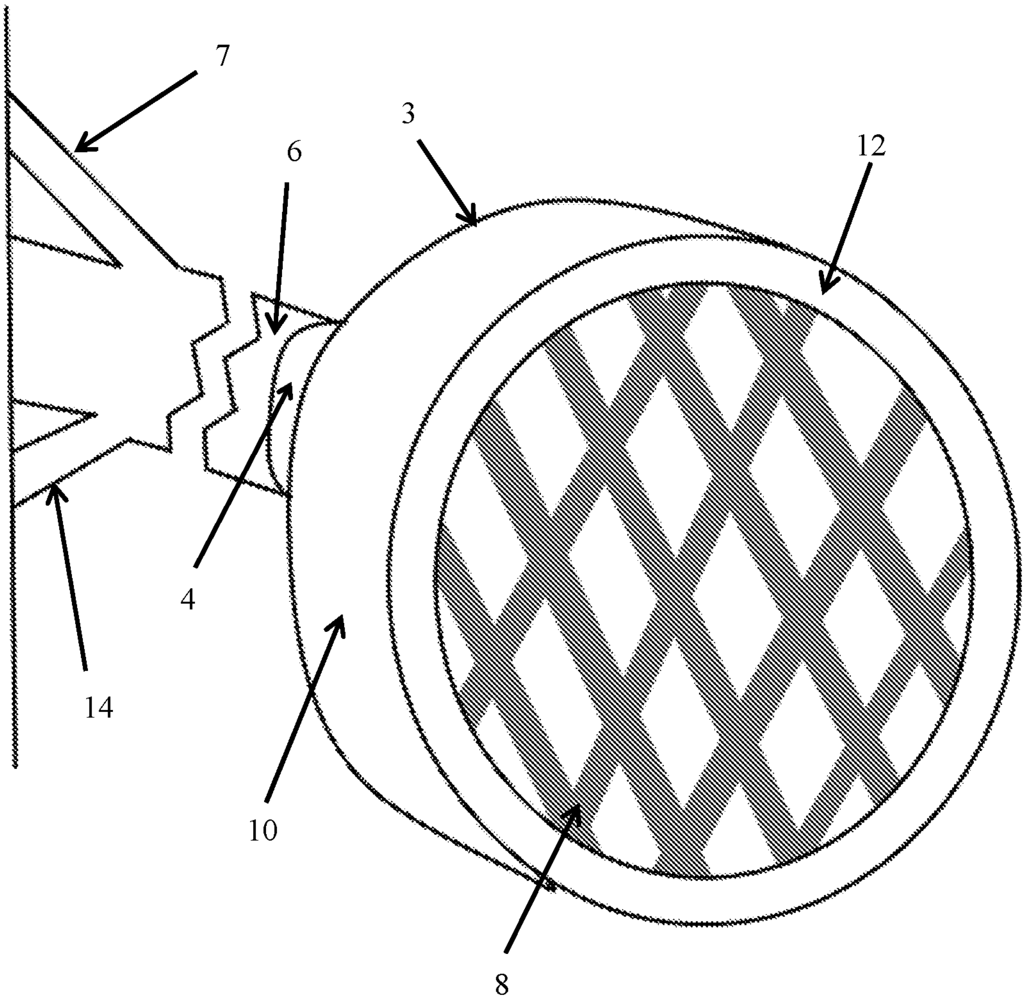
FIG. 2 shows a detailed view of a representative delivery component of a hemostatic agent applicator according to one embodiment.

FIG. 2 shows a detailed view of a representative delivery component (3) of the hemostatic agent applicator according to one embodiment. In some embodiments, the delivery component (3) is a suction cup, disc, or funnel. While the delivery component (3) depicted in FIG. 2 has circular shape, the delivery component (3) is not limited to circular shapes. It is possible to form an arbitrary shape (for example, an ellipse, an oval, a quadrangle such as a rectangle or a square, and a triangle) according to ease of use for a physician who, for example, performs surgery or a shape of a hemostatic agent application target area, as described below. In some embodiments, the delivery component (3) has a size and shape such that it substantially or completely covers a hemostatic agent application target area.

In some embodiments, the delivery component (3) is configured to be retractable within the distal end (6) of the handle (2). In some embodiments, the distal end (6) of the handle (2) has an expended diameter compared to the remaining portion of the handle (2) to accommodate the retraction of the delivery component (3) thereon. In some embodiments, the delivery component (3) is collapsible such that it can be retracted into the distal end (6) of the handle (2).

In some embodiments, the delivery component (3) is a circular suction cup having a diameter ranging from about 0.5 to about 5 cm, from about 1 to about 4.5 cm, from about 1.5 to about 4 cm, from about 2 to about 3.5 cm, from about 2.5 to about 3 cm, from about 0.5 to about 1 cm, from about 0.6 to about 0.9 cm, or from about 0.7 to about 0.8 cm. In some embodiments, the delivery component (3) is a circular suction cup having a diameter ranging from about 0.5 to about 5 cm. In some embodiments, the delivery component (3) is a circular suction cup having a diameter ranging from about 1.5 to about 4 cm. In some embodiments, the delivery component (3) is a circular suction cup having a diameter ranging from about 2 to about 3.5 cm. In some embodiments, the delivery component (3) is a circular suction cup having a diameter ranging from about 2.5 to about 3 cm. In some embodiments, the delivery component (3) is a circular suction cup having a diameter ranging from about 0.5 to about 1 cm. In some embodiments, the delivery component (3) is a circular suction cup having a diameter ranging from about 0.6 to about 0.9 cm. In some embodiments, the delivery component (3) is a circular suction cup having a diameter ranging from about 0.7 to about 0.8 cm.

As depicted in FIG. 1 and FIG. 2, the delivery component (3), such as a suction cup (but any form of the delivery component (3) such as a disc or funnel), is formed by a wall (10) provided to have a certain thickness, thereby forming an interior region. The wall (10) of the delivery component (3) comprises a base surface (12) on the lower region (on a distal side) of the wall (10). In some embodiments, the base surface (12) is flat. In some embodiments, the base surface (12) is subjected to a rounding process such that the delivery component (3) is atraumatic with respect to contact with the hemostatic agent application target area, as described below.

The shape of the interior region of the delivery component (3) may not necessarily be identical to the external shape of the delivery component (3). In some embodiments, the interior region has a hemispherical shape (as depicted in FIG. 2). In some embodiments, the interior region has an internal diameter in a range from about 0.3 cm to about 4.8 cm. The internal diameter is employed such that the hemostatic agent application target area is substantially covered or completely covered, as described below.

In some embodiments, the width of the base surface (12) need not be the same as the thickness of the wall (10). In some embodiments, the delivery component (3) further comprises a flange (13) (see, FIG. 1) extending from, for example, the base surface (12), of the wall (10), thereby providing for a wider contact surface. In some embodiments, the flange (13) extends inwardly, that is from the wall (10) toward the interior region of the delivery component (3). In some embodiments, the flange (13) extends outwardly from the wall (10). In some embodiments, the width of the flange (13) ranges from about 0.5 mm to about 5 mm, from about 0.6 mm to about 4.5 mm, from about 0.7 mm to about 4 mm, from about 0.8 mm to about 3.5 mm, from about 0.9 mm to about 3 mm, from about 1 mm to about 2.5 mm, or from about 1 mm to about 2 mm. In some embodiments, the width of the flange (13) ranges from about 0.5 mm to about 5 mm. In some embodiments, the width of the flange (13) ranges from about 0.6 mm to about 4.5 mm. In some embodiments, the width of the flange (13) ranges from about 0.7 mm to about 4 mm. In some embodiments, the width of the flange (13) ranges from about 0.8 mm to about 3.5 mm. In some embodiments, the width of the flange (13) ranges from about 0.9 mm to about 3 mm. In some embodiments, the width of the flange (13) ranges from about 1 mm to about 2.5 mm. In some embodiments, the width of the flange (13) ranges from about 1 mm to about 2 mm.

In some embodiments, the thickness of the flange (13) ranges from about 0.2 mm to about 1 mm, from about 0.3 mm to about 0.9 mm, from about 0.4 mm to about 0.8 mm, or from about 0.5 mm to about 0.7 mm. In some embodiments, the thickness of the flange (13) ranges from about 0.2 mm to about 1 mm. In some embodiments, the thickness of the flange (13) ranges from about 0.3 mm to about 0.9 mm. In some embodiments, the thickness of the flange (13) ranges from about 0.4 mm to about 0.8 mm. In some embodiments, the thickness of the flange (13) ranges from about 0.5 mm to about 0.7 mm.

In some embodiments, the handle (2) and the delivery component (3) are formed as a single piece. In some embodiments, the handle (2) and the delivery component (3) are separately formed and connected to each other at the distal end of the handle (6) by one or more cooperating connectors (4) or such that the two parts are attached. In some embodiments, the handle (2) and the delivery component (3) are rotationally attached, snapped together, or clipped together. In some embodiments, the handle (2) and the delivery component (3) are attached via a flexible joint, such as, but not limited to, a ball-and-socket joint, a gimbal joint, a hinge joint, or a pivot joint.

In some embodiments, the delivery component (3) is releasably attached to the distal end of the handle (6) via one or more cooperating connectors (4), wherein the delivery component (3) is configured to be released from the distal end (6) of the handle (2). Cooperating connectors (4) include, but are not limited to, snap connections, hook (e.g., hook and loop) fasteners, screw (e.g., screw threads), clips, ball and socket, spring, a sliding mechanism, and the like. In some embodiments the cooperating connector(s) (4) attaching the delivery component (3) to the distal end (6) of the handle (2) are configured to release the delivery component (3) when engaged by the first actuator (7).

In some embodiments, the handle (2) and the delivery component (3) may not necessarily be manufactured using the same material. For example, the handle (2) may be formed of a material suitable for repeated uses with different disposable delivery components (3), such as durable plastic or a metal alloy, whereas the delivery component (3) is manufactured using one or more bioabsorbable or biodegradable material (e.g., materials which are partially or completely absorbable and/or degradable in the body). Suitable biodegradable or bioabsorbable materials include, but are not limited to, chromic, polysaccharide, polyglycolide, poly(lactic acid), copolymers of lactic acid and glycolic acid, poly-L-lactide, poly-L-lactate; crystalline plastics such as those disclosed in U.S. Pat. No. 6,632,503; bioabsorbable polymers, copolymers or polymer alloys that are self-reinforced and contain ceramic particles or reinforcement fibers, such as those described in U.S. Pat. No. 6,406,498; bioresorbable polymers and blends thereof, such as described in U.S. Pat. No. 6,583,232; copolymers of polyethylene glycol and polybutylene terephthalate; and the like. The foregoing list is not intended to be exhaustive.

In some embodiments, the delivery component (3) is made of a transparent material for the ease of placement over the hemostatic agent application target area. Suitable transparent materials include, but are not limited to, transparent plastic materials, such as polymethylmethacrylates (PMMA), polyacrylates (PA), polycarbonates (PC), polyethylene terephthalates (PET), polyesters, styrene acrylonitrile copolymers (SAN), polystyenes (PS), acrylonitrile butadiene styrene (ABS), polyamide polymers (PA) such as Nylon™ type materials, and other known transparent plastics.

In some embodiments, the delivery component (3) may further comprise a hemostatic mesh, fiber, gel, liquid, semi-solid, or solid. In some embodiments, the hemostatic agent is pre-loaded into the interior region of the delivery component (3) upon manufacturing the delivery component (3). In some embodiments, the hemostatic agent is loaded into the interior region of the delivery component (3) just prior to its use. Hemostatic agents suitable for use with the hemostatic agent applicator (1) can be in the form of a gel, liquid, solid, paste, or powder. In some embodiments, the delivery component (3) pre-loaded with one or more hemostatic agents may be covered with a removable seal to be removed prior to use. The seal may prevent the hemostatic agent from flowing or spilling out of the delivery component (3). In some embodiments, the seal may prevent the hemostatic agent from scattering and obstructing the surgical field.

In some embodiments, the hemostatic agent is configured as a mesh or liquid bioglue or is attached to a mesh (8) (see, FIG. 2). Hemostatic meshes are described in, for example, U.S. Pat. No. 9,821,022. In some embodiments, the hemostatic mesh (8) is formed from one or more self-assembling peptides. The peptides can be in the form of fibers, such as nanofibers. The peptides can be assembled prior to formation of the mesh or after the mesh has been formed but before it is applied. Alternately, the mesh (8) can be prepared from unassembled peptides, which assemble at the time of the use of the applicator (1). The peptides can assemble upon contact with bodily fluids (e.g., blood) or can be contacted with an ionic solution to initiate assembly.

In some embodiments, the hemostatic agent is in an active form. In some embodiments, the hemostatic agent is in an inactive form, and is activated immediately prior to use. In some embodiments, the hemostatic agent is in a pre-active form, and is activated upon contact with target area, for example by contact with water, blood, or other components of the clotting cascade.

Numerous hemostatic agents are suitable for use with the applicators (1) disclosed herein. Any hemostatic agent that upon application to a wound reduces or stops blood loss by promoting blood clot formation can be used. In some embodiments, hemostatic agent includes, but are not limited to, natural and synthetic clay and silicate materials such as zeolite, kaolinite, and diatomaceous earth; glass and glass-ceramics; polymeric polysaccharides, such as algae and shellfish derived chitin, chitosan, and alginate; polymeric proteins, such as protamine sulfate; other polymers, such as polyacrylates; glass powders, beads or fibers, such as surface reactive glass-ceramics; small molecules, such as epsilon amino caproic acid; and plasma-derived or recombinant clotting factors, such as RGD peptide, thrombin, fibrinogen, fibrin, Factor V and/or Va, Factor VII and/or VIIa, Factor VIII and/or VIIIa, Factor IX and/or IXa, Factor X and/or Xa, Factor XI and/or XIa, Factor XII and/or XIIa, Factor XIII and/or XIIIa, or any combination thereof. In some embodiments, more than one hemostatic agent can he used. For example, a combination of two different hemostatic agents can be used. In some embodiments, the mesh (8) may comprise one hemostatic agent and another hemostatic agent may be used in the interior region of the delivery component (3). In some embodiments, the hemostatic agent is currently in common clinical use, such as, but not limited to, GELFOAM® (gelatin matrix), GELFILM® (gelatin matrix), SURGIFOAM® (gelatin matrix), SURGIFLO® (gelatin matrix), SURGICEL® FIBRILLAR™ (oxidized regenerated cellulose), SURGICEL® NU-KNIT® (oxidized regenerated cellulose), AVITENE™ (microfibrillar collagen), INSTAT® (microfibrillar collagen), HELITENE® (microfibrillar collagen), HELISTAT® (microfibrillar collagen), THROMIBIN-JMI® (topical bovine thrombin), RECOTHROM® (recombinant topical thrombin), EVITHROM® (topical human thrombin), rh Thrombin (recombinant human thrombin), FLOSEAL® (hemostatic matrix), EVICEL® (fibrin sealant), TISSEEL® (fibrin sealant), CROSSEAL® (fibrin sealant), TISSUCOL® (fibrin sealant), HEMASEEL® HMN (fibrin sealant), QUIXIL® (fibrin sealant), VIVOSTAT® (fibrin sealant), TACHOSIL® (fibrin sealant), or OXYCEL® (oxidized cellulose), or any combination thereof. When the hemostatic agent is disposed on the hemostatic agent application target area, the hemostatic agent is expected to easily infiltrate into a damaged tissue and permeate through to, for example, a fractured blood vessel.

In some embodiments, the delivery component (3) further comprises one or more tissue attachment members (15), which are configured to grip a wound or surface when the delivery component (3) is applied to the wound or target surface with pressure. In some embodiments, the tissue attachment members (15) may include a plurality of members, such as, but not limited to, barbs, points, needles, hooks, tines, rakes, wires, teeth, and bristles, or any combination thereof.

In some embodiments, the attachment members (15) are located on the flange (13) (see, FIG. 1). In some embodiments, the attachment members (15) are located on the surface of the flange (13) which faces the wound. In some embodiments, the tissue attachment members (15) are disposed circumferentially about the base surface (12). In some embodiments, the tissue attachment members (15) are disposed along a portion of the wall (10) of the delivery component (3) and are adopted to slide down toward tissue surface when pressure is applied. In some embodiments, the tissue attachment members (15) are deployed via engaging a mechanical actuator, for example a cord, a lever, a trigger slide, or a button. In some embodiments, the tissue attachment members (15) comprise a shape-memory or superelastic material. In some embodiments, the tissue attachment member (15) is an adhesion agent, such as tissue glue, applied to the base surface (12) or the surface of the flange (13) that faces the wound. The tissue glue can be any tissue-compatible matrix suitable for topical or other application to the site of treatment. The tissue glue can be a gel-like substance comprising pores within which the adhesion agent is held. It can be proteinaceous, and can be biodegradable. Suitable tissue glues include, but are not limited to, those disclosed in U.S. Pat. Nos. 5,552,452, 7,276,235, 8,197,506, 8,252,747; Kottai et al., Ann. Otol. Rhinol. Laryngol., 1983, 92, 29-32; Ronis et al., Laryngoscope, 1984, 94, 210-3; Barnstable, Nature, 1986, 321, 731-732; Toriumi et al., Otolaryngol. Clin. North Am., 1994, 27, 203-209; and Schlag et al., in Fibrin Sealant in Operative Medicine vol. 1, G. Schlag. 11. Redl (eds), Springer-Verlag Berlin-Heidelberg (1986) 27-38. In some embodiments, the tissue glue is thermally or chemically activatable.

In some embodiments, the tissue attachment members (15) are sutures, staples, or the like, which are used by, for example, a physician at the time of treating a patient. In some embodiments, the sutures or staples can be placed through the wall (10) of the delivery component (3), through the base surface (12), or through the flange (13) into the wound tissue. In some embodiments, the sutures and staples are made of biodegradable and/or bioabsorbable materials.

As stated herein, the handle (2) of the applicator (1) comprises a first actuator (7). In some embodiments, first actuator (7) is located at the proximal portion (5) of the handle (2) (see, FIG. 1). In some embodiments, the first actuator (7) is located in the middle portion of the handle (2). The first actuator (7) is configured to, upon engagement, release the delivery component (3) from the distal end (6) of the handle (2). In some embodiments, the first actuator (7) is configured to retract and/or deploy the delivery component (3) from within the distal end (6) of the handle (2). A suitable first actuator (7) includes, but is not limited to, a button, a cord, a slide, a snap, a screw, or a lever. In some embodiments, the first actuator (7) is configured to be activated manually, mechanically, electrically, or pneumatically. In some embodiments, the first actuator (7) is enclosed within the handle (2) and is remotely operated.

The handle (2) of the applicator (1) also comprises a second actuator (14). In some embodiments, second actuator (14) is located at the proximal portion (5) of the handle (2) (see, FIG. 1). In some embodiments, the second actuator (14) is located in the middle portion of the handle (2). The second actuator (14) is configured to, upon engagement, release any contents of the delivery component (3). A suitable second actuator (14) includes, but is not limited to, a button, a cord, a slide, a snap, a screw, or a lever. In some embodiments, the second actuator (14) is configured to be activated manually, mechanically, electrically, or pneumatically. In some embodiments, the second actuator (14) is enclosed within the handle (2) and is remotely operated. The first actuator (7) and the second actuator (14) need not be the same type (e.g., the first actuator (7) can be a button whereas the second actuator (14) can be a lever).

In some embodiments, the applicator (1) is configured to deliver the hemostatic agent on contact with the hemostatic agent application target area. In some embodiments, the applicator (1) is configured to release or extrude the hemostatic agent from the interior region of the delivery component (3) via engaging the second actuator (14) which is in communication with the delivery component (3). In some embodiments, the second actuator (14) is configured to be activated manually, mechanically, electrically, or pneumatically. In some embodiments, the applicator (1) is also configured to release the delivery component (3) at the site of the wound in contact with the hemostatic agent application target area. In some embodiments, the applicator (1) is configured to release the delivery component (3) via engaging the first actuator (7) which is in communication with the delivery component (3). In some embodiments, the first actuator (7) is configured to be activated manually, mechanically, electrically, or pneumatically.

The present disclosure also provides kits comprising one or more hemostatic agent applicators (1). In some embodiments, the handle (2) of the hemostatic agent applicator (1) is disposable. In some embodiments, the handle (2) of the hemostatic agent applicators (1) is reusable. In some embodiments, the kit comprises a single reusable handle (2) and one or more delivery components (3). The handle (2) and the delivery components (3) can be packed together within the kit or can be packaged separately within the kit. The one or more delivery components (3) can be packed together or each delivery component (3) can be packaged separately. In some embodiments, the packaging is sterile. In some embodiments, the kit comprises empty delivery components (3) to be loaded with hemostatic agents prior to use. In some embodiments, the kit further comprises one or more containers containing one or more hemostatic agents to be loaded into a delivery component (3) prior to use. In some embodiments, the kit comprises one or more containers of the same hemostatic agent. In some embodiments, the kit comprises one or more containers of different hemostatic agents. In some embodiments, the kit comprises one or more containers of a pre-formed mixture of two or more hemostatic agents. In some embodiments, the kit further comprises a container comprising an activating agent, such as described above, to be mixed with an inactive or pre-active hemostatic agent prior to use. In some embodiments, the kit further comprises one or more tissue attachment members (15), such as an adhesive agent for attaching the delivery component (3) to the hemostatic agent application target area, such as a glue, or sutures or staples. Each kit may also include printed instructions and/or a printed label describing the methods of using the applicator (1). In some embodiments, some or all of the kit components can be sterile.

The present disclosure also provides methods of using the hemostatic agent applicator (1) (such as any of those disclosed herein) comprising: a) contacting a bleeding or weakened wound or surface of a patient with the delivery component (3) of the hemostatic agent applicator (1); b) applying manual pressure to the surface or wound, wherein the delivery component (3) comprises one or more hemostatic meshes (8) or contains one or more hemostatic agents, or both; c) maintaining the contact and the pressure for a time sufficient for hemostasis to begin; and d) optionally, releasing the delivery component (3) from the handle (2) by engaging the first actuator (7) of the applicator (1), thereby leaving the delivery component (3) contacting the surface or wound (i.e., the hemostatic agent application target area).

The methods described herein contemplate the use of the hemostatic agent applicator (1) on multiple types of target surfaces (i.e., hemostatic agent application target area). In some embodiments, the hemostatic agent application target area includes, but is not limited to, cutting wounds, tearing wounds, crushing wounds, burn wounds, puncture wounds, pathology-associated wounds (e.g., sores), and surgical incisions. In some embodiments, the applicator (1) can be used on any surface having a structural disturbance that results or may result in bleeding. The hemostatic agent application target areas can be located internally or externally on the patient.

In some embodiments when the one or more hemostatic agents is preactive or inactive, the method further comprises activating the one or more hemostatic agents prior to contacting the bleeding or weakened wound or surface of the patient with the delivery component (3). In some embodiments when the one or more hemostatic agents is preactive or inactive, the method further comprises activating the one or more hemostatic agents upon contacting the bleeding or weakened wound or surface of the patient with the delivery component (3).

In some embodiments, the method further comprises releasing or extruding the one or more hemostatic agents from the delivery component (3) by engaging the second actuator (14) prior to releasing the delivery component (3) from the handle (2), thereby bringing the one or more hemostatic agents into contact with the hemostatic agent application target area. In some embodiments, releasing or extruding the one or more hemostatic agents from the delivery component (3) can be similar to the top or tip of a dart being deployed via a trigger mechanism, an unscrewing motion, or an unclamping.

In some embodiments, the method further comprises attaching the delivery component (3) to the surface of the wound prior to releasing the delivery component (3) from the handle (2). In some embodiments, the delivery component (3) is attached to the surface or the wound by one or more tissue attachment members (15), such as a glue, one or more sutures, one or more bristles, one or more hooks, one or more clips, or one or more staples, as described herein. In some embodiments, the glue is thermally or chemically activated.

In some embodiments, the method further comprises attaching the delivery component (3) to the distal end (6) of the handle (2) of the hemostatic agent applicator (1) prior to contacting the bleeding or weakened wound or surface of the patient with the delivery component (3). In some embodiments, the method further comprises deploying a retracted delivery component (3) from within the distal end (6) of the handle (2) of the hemostatic agent applicator (1) prior to contacting the bleeding or weakened wound or surface of the patient with the delivery component (3).

In embodiments in which the delivery component (3) is manufactured from biodegradable or bioabsorbable materials, the method may comprise leaving the attached or deployed delivery component (3) at the hemostatic agent application target area until it degrades or is absorbed by the body. In embodiments where the hemostatic agent application target area is internal (e.g., surgery related), the method further comprises adhering or attaching the delivery component (3) manufactured from biodegradable or bioabsorbable materials to the hemostatic agent application target area and suturing or otherwise closing the outer tissue layers above, thereby leaving delivery component (3) inside the patient's body until it degrades or is absorbed by the body.

In embodiments in which the delivery component (3) is manufactured from non-biodegradable or non-bioabsorbable materials, the method may comprise maintaining the contact and the pressure of the delivery component (3) on the hemostatic agent application target area for a time sufficient for hemostasis to begin, as determined by the operator; disengaging the delivery component (3) from the target area and subsequently removing the delivery component (3) from the patient.

In embodiments in which the hemostatic agent applicator (1) or handle (2) thereof is reusable, the method can further comprise sterilization of the applicator (1) or handle (2) thereof after each use, and, optionally, subsequently reloading the delivery component (3) with hemostatic agent(s) for the next use.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:

1. A hemostatic agent applicator comprising:

a handle having a proximal portion and a distal end; and a delivery component releasably coupled to the distal end of the handle, wherein the delivery component comprises a hemostatic agent, wherein the delivery component further comprises one or more tissue attachment members configured to grip a wound or surface when the delivery component is applied to the wound or surface with pressure, wherein each tissue attachment member of the one or more tissue attachment members is at least one of: one or more barbs, one or more points, one or more needles, one or more hooks, one or more tines, one or more rakes, one or more wires, one or more teeth, one or more adhesion agent, one or more staples, or one or more sutures, and wherein the delivery component is configured to release the hemostatic agent when the delivery component is applied to the wound or surface.

2. The applicator according to claim 1, wherein the handle is flexible and/or steerable.

3. The applicator according to claim 1, wherein the delivery component is a suction cup, disc, or funnel.

4. The applicator according to claim 1, wherein the hemostatic agent is at least one of a liquid, a gel, a paste, a solid, a glue, a bioadhesive, or a powder, or is a mesh or deployed on a mesh.

5. The applicator according to claim 1, wherein the distal end of the handle and the delivery component are rotationally attached, or snapped together, or clipped together.

6. The applicator according to claim 1, wherein the delivery component is attached to the distal end of the handle by one or more cooperating connectors, wherein the one or more cooperating connectors are configured to release the detachable delivery component.

7. The applicator according to claim 6, wherein the one or more cooperating connectors is a hook, sliding mechanism, ball and socket, spring, or screw.

8. A kit comprising:

one or more hemostatic agent applicators, wherein each applicator of the one or more hemostatic agent applicators comprises a handle having a proximal portion and a distal end; and one or more delivery components, wherein each delivery component of the one or more delivery components comprises a hemostatic agent and is configured to be releasably coupled to the distal end of the handle of an applicator of the one or more hemostatic agent applicators;

wherein each delivery component of the one or more delivery components comprises one or more tissue attachment members configured to grip a wound or surface when the delivery component is applied to the wound or surface with pressure, wherein each tissue attachment member of the one or more tissue attachment members is at least one of: one or more barbs, one or more points, one or more needles, one or more hooks, one or more tines, one or more rakes, one or more wires, one or more teeth, one or more adhesion agent, one or more staples, or one or more sutures, and wherein each delivery component of the one or more delivery components is configured to release the hemostatic agent when the delivery component is applied to the wound or surface.

9. The kit according to claim 8, wherein the delivery component is attached to the distal end of the handle by one or more cooperating connectors, wherein the one or more cooperating connectors are configured to release the delivery component.

10. The kit according to claim 8, wherein the delivery component is a suction cup, disc, or funnel.

11. A method of using the hemostatic agent applicator according to claim 1 comprising:

a) contacting a bleeding or weakened wound or surface of a patient with the delivery component of the hemostatic agent applicator;

b) applying manual pressure to the surface or wound, wherein the delivery component comprises one or more hemostatic meshes or contains one or more hemostatic agents, or both; and c) maintaining the contact and the pressure for a time sufficient for hemostasis to begin.

12. The method according to claim 11, releasing the delivery component from the handle, thereby leaving the delivery component contacting the wound or surface.

13. The method according to claim 11, further comprising attaching the delivery component to the surface of the wound prior to releasing the delivery component from the handle.

14. The method according to claim 12, further comprising releasing the one or more hemostatic agents from the delivery component prior to releasing the delivery component from the handle.

* * * * *